(12) United States Patent
Madokoro et al.

(10) Patent No.: US 8,710,464 B2
(45) Date of Patent: Apr. 29, 2014

(54) SPECIMEN PREPARATION DEVICE, AND CONTROL METHOD IN SPECIMEN PREPARATION DEVICE

(75) Inventors: Yuichi Madokoro, Hitachinaka (JP); Tsuyoshi Onishi, Hitachinaka (JP); Megumi Aizawa, Hitachi (JP); Yukio Yoshizawa, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 276 days.

(21) Appl. No.: 13/203,807

(22) PCT Filed: Oct. 23, 2009

(86) PCT No.: PCT/JP2009/005580
§ 371 (c)(1),
(2), (4) Date: Aug. 29, 2011

(87) PCT Pub. No.: WO2011/116428
PCT Pub. Date: Oct. 14, 2010

(65) Prior Publication Data
US 2011/0309245 A1 Dec. 22, 2011

(30) Foreign Application Priority Data
Mar. 30, 2009 (JP) ................................. 2009-080851

(51) Int. Cl.
*G21K 5/08* (2006.01)
(52) U.S. Cl.
USPC ................ 250/492.21; 250/492.1; 250/492.2; 250/492.3; 250/306; 250/310
(58) Field of Classification Search
USPC ................ 250/310, 492.21, 492.11, 311, 307
See application file for complete search history.

(56) References Cited

U.S. PATENT DOCUMENTS

| 6,794,663 | B2 * | 9/2004 | Shichi et al. ............. 250/492.21 |
| 7,397,052 | B2 * | 7/2008 | Tomimatsu et al. ...... 250/492.21 |
| 7,897,936 | B2 * | 3/2011 | Shichi et al. ............. 250/442.11 |
| 8,405,053 | B2 * | 3/2013 | Tomimatsu et al. ..... 250/492.21 |
| 2003/0184332 | A1 | 10/2003 | Tomimatsu et al. |
| 2005/0269511 | A1 * | 12/2005 | Tomimatsu et al. .......... 250/310 |
| 2006/0138323 | A1 * | 6/2006 | Chang et al. .................. 250/307 |

(Continued)

FOREIGN PATENT DOCUMENTS

| EP | 1 335 209 A1 | 8/2003 |
| EP | 1 870 691 A2 | 12/2007 |

(Continued)

*Primary Examiner* — Nikita Wells
*Assistant Examiner* — Johnnie L Smith
(74) *Attorney, Agent, or Firm* — McDermott Will & Emery LLP

(57) ABSTRACT

Separation and the like of an excised specimen from a specimen are automatically performed. Marks for improving image recognition accuracy are provided in a region that becomes an excised specimen in a specimen and a region other than said region, or in a transfer means for transferring the excised specimen and a specimen holder capable of holding the excised specimen, and the relative movement of the excised specimen and the specimen, and the like are recognized with high accuracy by image recognition. In the sampling of a minute specimen using a focused ion beam, the detection of an end point of processing for separation of the excised specimen from the specimen, and the like are automatically performed. Thus, for example, unmanned specimen excision becomes possible, and preparation of a lot of specimens becomes possible.

25 Claims, 16 Drawing Sheets

(56) References Cited

U.S. PATENT DOCUMENTS

| | | | |
|---|---|---|---|
| 2006/0226359 A1* | 10/2006 | Principe | 250/310 |
| 2008/0073535 A1 | 3/2008 | Hong et al. | |
| 2008/0289954 A1 | 11/2008 | Kaito | |

FOREIGN PATENT DOCUMENTS

| | | |
|---|---|---|
| JP | 09-306402 | 11/1997 |
| JP | 2774884 | 7/1998 |
| JP | 2000-251820 | 9/2000 |
| JP | 2002-040107 | 2/2002 |
| JP | 2002-150983 | 5/2002 |
| JP | 3547143 | 7/2004 |
| JP | 3695181 | 9/2005 |
| JP | 2005-345347 | 12/2005 |
| JP | 2007-108042 | 4/2007 |
| JP | 2007-194096 | 8/2007 |
| JP | 2008-026312 | 2/2008 |
| JP | 2008-122114 | 5/2008 |
| WO | WO 02/08774 A1 | 1/2002 |

* cited by examiner

EXCISING SPECIMEN

SPECIMEN PREPARATION DEVICE, AND CONTROL METHOD IN SPECIMEN PREPARATION DEVICE

RELATED APPLICATIONS

This application is the U.S. National Phase under 35 U.S.C. §371 of International Application No. PCT/JP2009/005580, filed on Oct. 23, 2009, which in turn claims the benefit of Japanese Application No. 2009-080851, filed on Mar. 30, 2009, the disclosures of which Applications are incorporated by reference herein.

TECHNICAL FIELD

The present invention relates to method of excising a minute region of a specimen by means of a focused ion beam.

BACKGROUND ART

In U.S. Pat. No. 2,774,884 (Patent Literature 1), a part of a specimen substrate is processed by means of sputtering of a focused ion beam to be made a cantilever shape, a probe is brought into contact with a part of an excising specimen and is bonded thereto by a FIB induced deposition film, a connecting portion of the excising specimen and the specimen substrate is subjected to sputtering, and the excising specimen is separated from the specimen substrate.

In U.S. Pat. No. 3,547,143 (Patent Literature 2) and U.S. Pat. No. 3,695,181 (Patent Literature 3), a minute specimen excised by a focused ion beam is transferred to a specimen holder arranged in a specimen chamber, and the specimen holder and the minute specimen are bonded together by a FIB induced deposition film. Also, there is disclosed that before a minute specimen is excised by a focused ion beam, a mark, which specifies a region being observed, is provided on a specimen substrate.

CITATION LIST

Patent Literature

Patent Literature 1: U.S. Pat. No. 2,774,884
Patent Literature 2: U.S. Pat. No. 3,547,143
Patent Literature 3: U.S. Pat. No. 3,695,181

SUMMARY OF INVENTION

Technical Problem

Having earnestly examined automation of method of excising a minute region of a specimen using a focused ion beam, the inventors of the present application have gotten the following knowledge.

In Patent Literatures 1 to 3, there is not described concrete method, in which a focused ion beam device automatically carries out a process of subjecting a connecting portion of an excising specimen and a specimen substrate to sputtering to separate the excising specimen from the specimen substrate. Also, in case of carrying out the process through a personal's judgment, it becomes difficult to improve a yield beyond a certain extent.

Further, when an end point of the processing for separation cannot be detected automatically, there is a possibility that when a probe is moved to transfer an excising specimen from a specimen substrate, a bonded portion having not been completely separated peels off and the specimen substrate falls off.

An object of the invention concerns automatically performing separation and the like of an excising specimen from a specimen.

Solution to Problem

The invention relates to providing marks, for improvement of image recognition accuracy, in a region that becomes an excising specimen in a specimen and another region other than said region, or in transfer means for transferring the excising specimen and a specimen holder capable of holding the excising specimen, and recognizing the relative movement of the excising specimen and the specimen with high accuracy by image recognition.

Advantageous Effect of Invention

According to the invention, in sampling of a minute specimen using a focused ion beam, it is possible to automatically perform detection of an end point of the processing for separation of an excising specimen from a specimen. Thus, for example, unmanned specimen excision becomes possible, and preparation of a lot of excising specimens becomes possible.

DESCRIPTION OF EMBODIMENTS

Figure 1:
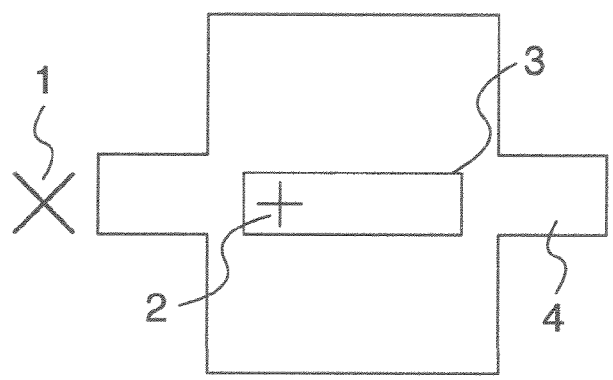
FIG. 1 is a plan view showing a mark on a substrate and a mark on an excising specimen part.

An embodiment discloses a specimen preparation device comprising: a specimen stage on which a specimen is mounted, an ion beam optical system adapted to irradiate an ion beam; transfer means adapted to transfer an excising specimen separated from the specimen by means of ion beam irradiation; and an arithmetic unit adapted to control the ion beam optical system, and wherein when the ion beam is irradiated on the specimen to separate the excising specimen from the specimen, a mark formed in a region, which makes the excising specimen, on the specimen and another mark formed in another region other than the region are measured and the ion beam irradiation is stopped in the case where a relative position between the marks is put in a predetermined condition.

Also, an embodiment discloses a specimen preparation device comprising: a specimen stage on which a specimen is mounted; an ion beam optical system adapted to irradiate an ion beam; transfer means adapted to transfer an excising specimen separated from the specimen by means of ion beam irradiation; and an arithmetic unit adapted to control the ion beam optical system, and wherein when an ion beam is irradiated on the specimen to separate the excising specimen from the specimen, a mark formed on the transfer means holding a region, which makes the excising specimen, on the specimen and another mark formed in another region other than the region, which makes the excising specimen, on the specimen are measured and the ion beam irradiation is stopped in the case where a relative position between the marks is put in a predetermined condition.

Also, an embodiment discloses a specimen preparation device comprising: a specimen stage on which a specimen is mounted; an ion beam optical system adapted to irradiate an ion beam; transfer means adapted to transfer an excising specimen separated from the specimen by means of ion beam irradiation; and an arithmetic unit adapted to control the ion beam optical system, and wherein when the transfer means is moved and brought into contact with the excising specimen, a mark formed on the transfer means and another mark formed in a region, which makes the excising specimen, on the specimen are measured and the transfer means is stopped in the case where a relative position between the marks is put in a predetermined condition.

Also, an embodiment discloses a specimen preparation device comprising: a specimen stage on which a specimen is mounted; an ion beam optical system adapted to irradiate an ion beam; transfer means adapted to transfer an excising specimen separated from the specimen by means of ion beam irradiation; and an arithmetic unit adapted to control the ion beam optical system, and wherein when the transfer means is moved and brought into contact with the excising specimen, a mark formed on the transfer means and another mark formed in a region other than another region, which makes the excising specimen, on the specimen are measured and the transfer means is stopped in the case where a relative position between the marks is put in a predetermined condition.

Also, an embodiment discloses a specimen preparation device comprising: a specimen stage on which a specimen is mounted; an ion beam optical system adapted to irradiate an ion beam; transfer means adapted to transfer an excising specimen separated from the specimen by means of ion beam irradiation; a specimen holder adapted to hold the excising specimen; and an arithmetic unit adapted to control the ion beam optical system, and wherein when the excising specimen held on the transfer means is transferred to the specimen holder, a mark formed on the excising specimen and a mark formed on the specimen holder are measured and movement of the transfer means is stopped in the case where a relative position between the marks is put in a predetermined condition.

Also, an embodiment discloses a specimen preparation device comprising: a specimen stage on which a specimen is mounted, an ion beam optical system adapted to irradiate an ion beam; transfer means adapted to transfer an excising specimen separated from the specimen by means of ion beam irradiation; a specimen holder adapted to hold the excising specimen; and an arithmetic unit adapted to control the ion beam optical system, and wherein when the excising specimen held on the transfer means is transferred to the specimen holder, a mark formed on the transfer means for transferring the specimen and a mark formed on the specimen holder are measured and movement of the transfer means is stopped in the case where a relative position between the marks is put in a predetermined condition.

Also, an embodiment discloses control method in a specimen preparation device comprising: a specimen stage on which a specimen is mounted, an ion beam optical system adapted to irradiate an ion beam; transfer means adapted to transfer an excising specimen separated from the specimen by means of ion beam irradiation; and an arithmetic unit adapted to control the ion beam optical system, wherein when an ion beam is irradiated on the specimen to separate the excising specimen from the specimen, a mark formed in a region, which makes the excising specimen, on the specimen and another mark formed in another region other than the region are measured and the ion beam irradiation is stopped in the case where a relative position between the marks is put in a predetermined condition.

Also, an embodiment discloses control method in a specimen preparation device comprising: a specimen stage on which a specimen is mounted, an ion beam optical system adapted to irradiate an ion beam; transfer means adapted to transfer an excising specimen separated from the specimen by means of ion beam irradiation; and an arithmetic unit adapted to control the ion beam optical system, wherein when an ion beam is irradiated on the specimen to separate the excising specimen from the specimen, a mark formed on the transfer means holding a region, which makes the excising specimen, on the specimen and another mark formed in another region other than the region, which makes the excising specimen, on the specimen are measured and the ion beam irradiation is stopped in the case where a relative position between the marks is put in a predetermined condition.

Also, an embodiment discloses control method in a specimen preparation device comprising: a specimen stage on which a specimen is mounted; an ion beam optical system adapted to irradiate an ion beam; transfer means adapted to transfer an excising specimen separated from the specimen by means of ion beam irradiation; and an arithmetic unit adapted to control the ion beam optical system, wherein when the transfer means is moved and brought into contact with the excising specimen, a mark formed on the transfer means and a mark formed in a region, which makes the excising specimen, on the specimen are measured and the transfer means is stopped in the case where a relative position between the marks is put in a predetermined condition.

Also, an embodiment discloses control method in a specimen preparation device comprising: a specimen stage on which a specimen is mounted; an ion beam optical system adapted to irradiate an ion beam; transfer means adapted to transfer an excising specimen separated from the specimen by means of ion beam irradiation; and an arithmetic unit adapted to control the ion beam optical system, wherein when the transfer means is moved and brought into contact with the excising specimen, a mark formed on the transfer means and a mark formed in a region other than another region, which makes the excising specimen, on the specimen are measured and the transfer means is stopped in the case where a relative position between the marks is put in a predetermined condition.

Also, an embodiment discloses control method in a specimen preparation device comprising: a specimen stage on which a specimen is mounted; an ion beam optical system adapted to irradiate an ion beam; transfer means adapted to transfer an excising specimen separated from the specimen by means of ion beam irradiation; a specimen holder adapted to hold the excising specimen; and an arithmetic unit adapted to control the ion beam optical system, wherein when the excising specimen held on the transfer means is transferred to the specimen holder, a mark formed on the excising specimen and a mark formed on the specimen holder are measured and movement of the transfer means is stopped in the case where a relative position between the marks is put in a predetermined condition.

Also, an embodiment discloses control method in a specimen preparation device comprising: a specimen stage on which a specimen is mounted; an ion beam optical system adapted to irradiate an ion beam; transfer means adapted to transfer an excising specimen separated from the specimen by means of ion beam irradiation; a specimen holder adapted to hold the excising specimen; and an arithmetic unit adapted to control the ion beam optical system, wherein when the excising specimen held on the transfer means is transferred to the specimen holder, a mark formed on the transfer means for transfer of the excising specimen and a mark formed on the specimen holder are measured and movement of the transfer means is stopped in the case where a relative position between the marks is put in a predetermined condition.

Also, the embodiments disclose that the specimen preparation device comprises an electron beam column adapted to irradiate an electron beam and the marks are measured by the electron beam.

Also, the embodiments disclose that an ion beam condition in measuring the marks can be changed to an ion beam condition in processing a specimen.

Also, the embodiments disclose that the ion beam comprises a focused ion beam. Also, there is disclosed that the ion beam comprises a projection-type ion beam.

Also, the embodiments disclose that the transfer means comprises a probe. Also, there is disclosed that a region on the probe to be brought into contact with the excising specimen, is provided with a step. Also, there is disclosed that the probe includes at a tip end thereof two or more steps aligned in an axial direction of the probe. Also, there is disclosed that the probe includes at a tip end thereof at least two or more steps aligned in a direction substantially perpendicular to the axial direction of the probe.

Also, the embodiments disclose that the transfer means comprises a micro manipulator.

Also, the embodiments disclose that the specimen stage and/or the transfer means are/is finely driven so that pressure is generated between the excising specimen and the transfer means.

Also, the embodiments disclose that relative parallel movement and/or relative inclined movement of the specimen stage and the transfer means are/is made so that pressure is generated between the excising specimen and the transfer means.

Also, the embodiments disclose that the probe is rotated about an axis of the probe so that pressure is generated between the excising specimen and the probe.

Also, the embodiments disclose that an ion beam is irradiated on the specimen to prepare a mark formed in a region, which makes the excising specimen, on the specimen and/or another mark formed in another region other than the region which makes the excising specimen, on the specimen.

The above matter and other novel features and effects will be described hereinafter with reference to the drawings. In addition, the drawings are used for the sake of understanding of the invention and do not restrict the scope of the right. Further, respective embodiments can be combined appropriately and such combined configurations are disclosed in the specification of the present application.

Embodiment 1

Figure 41:
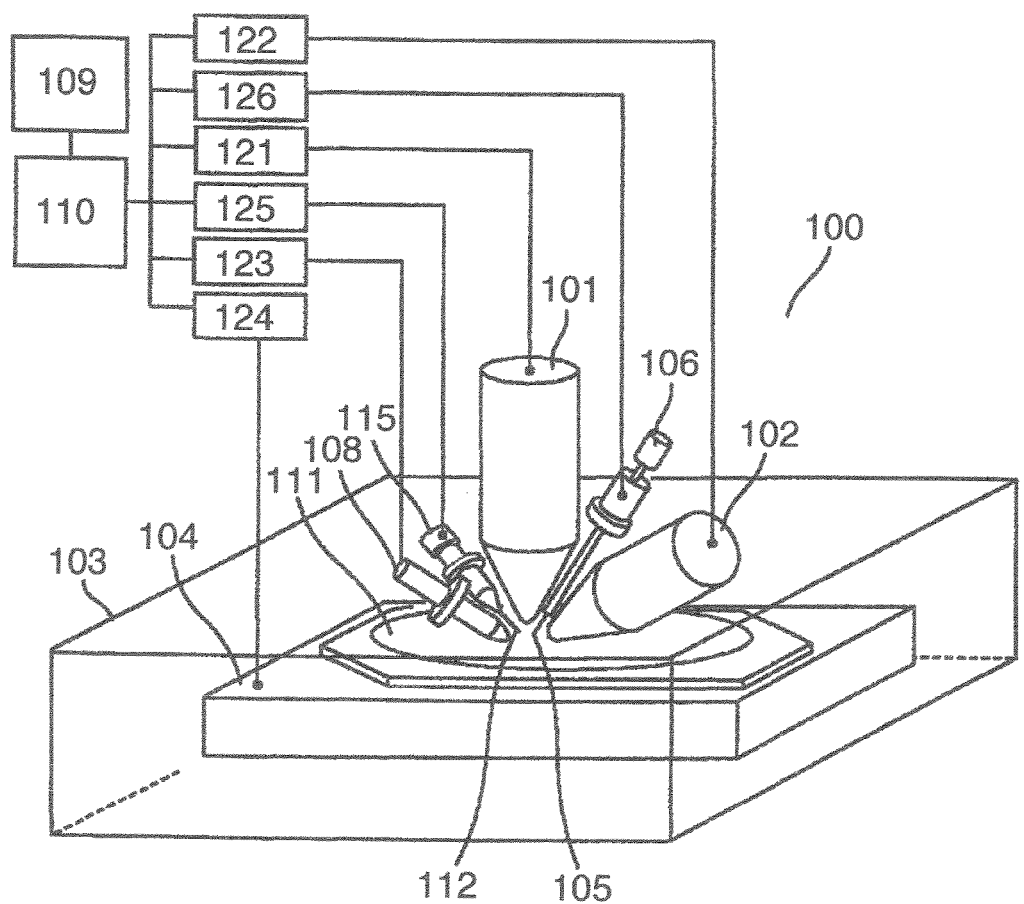
FIG. 41 is a schematic view showing a charged particle beam device.

FIG. 41 is a schematic view showing a charged particle beam device in an embodiment to depict an interior of a part of the device in perspective.

A charged particle beam device 100 comprises a focused ion beam column 101 for generating ion beams for observation and processing of a specimen and a probe, an electron beam column 102 for generating electron beams for observation of surface shapes of the specimen and the probe, a vacuum specimen chamber 103, a specimen stage 104, on which a specimen is put, a probe driving unit 106 for fine movement of the probe 105 in the vacuum specimen chamber 103, a detector 108, a deposition gas source 115, a display 109, and an arithmetic processing unit 110.

The focused ion beam column 101 forms ions generated in an ion source (not shown) into a beam form to irradiate the same on a specimen 111 and the probe 105, thereby enabling observing or processing surfaces of the specimen 111 and the probe 105. Also, the electron beam column 102 forms electrons generated in an electronic source (not shown) into a beam form to irradiate the same on the specimen 111 and the probe 105, thereby enabling observing the surfaces of the specimen 111 and the probe 105. By arranging the both columns so that a position of irradiation of electron beams from the electron beam column 102 is made the same as a position of irradiation of ion beams from the focused ion beam column 101, it is possible to observe a portion processed by ion beams with the use of electron beams. In FIG. 41, the focused ion beam column 101 is arranged in a vertical direction and the electron beam column 102 is arranged in a slant direction to a horizontal plane. However, this arrangement is not limitative but, for example, the electron beam column 102 may be arranged in the vertical direction and the focused ion beam column 101 may be arranged in the slant direction to the horizontal plane. Also, instead of focused ion beams, a projection-type ion beam device may be used. Also, a single column focused ion beam device provided with no electron beam column, and a triple column device further including a gaseous ion beam column such as argon or the like will do.

The specimen stage 104 can put thereon a specimen 111 to enable moving a location, which is necessary for processing and observation of ion beams, to an ion beam irradiated position and to a position of observation with electron beams. In addition, there are assumed, as the specimen 111, iron steel, light metal, and a polymer base high polymer, or the like in addition to semiconductor specimens.

The probe 105 can be moved by the probe driving unit 106 in the vacuum specimen chamber 103 and is made use of in excising a minute specimen piece formed on a specimen and in contacting with a specimen surface to give an electric potential to the specimen. The deposition gas source 115 stores deposition gases for formation of a deposited film upon irradiation of charged particle beams to enable the same to be supplied from a nozzle tip end 112 in response to needs. In addition, instead of the probe, there may be used a micro fork capable of holding a minute specimen piece between tip ends thereof and a micro manipulator, such as robot arms, etc., capable of grasping a minute specimen piece.

The detector 108 is one for secondary electrons and secondary ions, which are generated from irradiated portions of a specimen and a probe by irradiation of ion beams and electron beams, back-scattering electrons, X-rays, reflection electron, etc. Detection signals are subjected to arithmetic processing by the arithmetic processing unit 110 to be formed into an image and the display 109 displays a secondary electron image, a secondary ion image, an element map formed by a characteristic X-ray, etc. Also, transmission electrons may be converted into secondary electrons to be detected by the detector 108, and a detector (not shown) may be also used to detect transmission electrons. Also, the arithmetic processing unit 110 can control the focused ion beam column 101, the electron beam column 102, the detector 108, the specimen stage 104, the deposition gas source 115, and the probe driving unit 106, respectively, through ion beam control means 121, electron beam control means 122, detector control means 123, stage control means 124, deposition gas source control means 125, and probe control means 126.

An explanation will be given to excision of a specimen by means of focused ion beams in the embodiment. FIGS. 1 to 6 are views as viewed from just above a specimen and FIGS. 9 to 14 are cross sectional views.

FIG. 1 shows a state, in which an on-substrate mark 1 is detected by means of image recognition with a specimen kept horizontal, a periphery of a specimen excising part 3 is subjected to automatic sputtering on relative coordinates registered relative to the on-substrate mark 1, and formation of a peripherally processed hole 4 is completed. The specimen excising part 3 is in the form of a thin wall connected only on a bottom side to the substrate.

In the embodiment, a relative position of an on-specimen mark 2 relative to the on-substrate mark 1 is beforehand determined and after formation of the on-substrate mark 1, the on-specimen mark 2 is subjected to automatic processing on the specimen excising part 3 on the basis of the on-substrate mark 1. However, this is not limitative but the on-substrate mark 1 and the on-specimen mark 2 may be processed together. In addition, while the marks are prepared by means of sputtering with irradiation of focused ion beams, they may be prepared by means of deposition processing or the like. Any mark shapes will do provided that they are sized to afford processing on a specimen and made definite, and a cross mark is adopted in the embodiment. In addition, in the case where there exists a similar shape on a specimen surface, a different mark shape will do in consideration of erroneous detection.

After the processing, an image of the on-specimen mark 2 is acquired. Since a position of the on-substrate mark 1 is registered at the time of automatic processing, an image of the on-specimen mark 2 is acquired to result in registration of relative position of the on-substrate mark 1 and the on-specimen mark 2. While the on-substrate mark 1 and the on-specimen mark 2 are the same position in an up and down direction in FIG. 1, this is not necessarily important but the marks are not required to be put in a specific positional relationship provided that they are included in the same scanning range. Also, the marks can be replaced by definite characteristic items, which are beforehand existent on the substrate.

Figure 2:
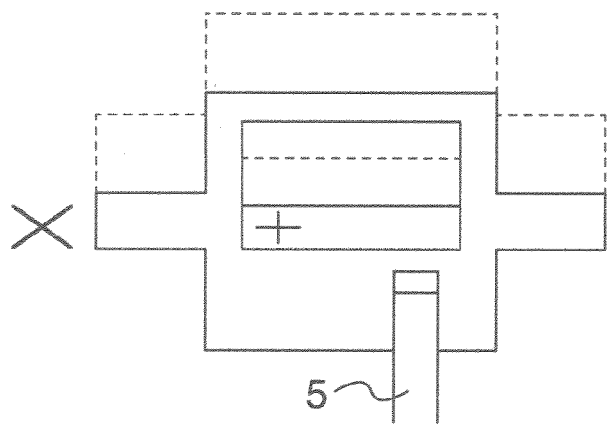
FIG. 2 shows an image observed from above when a probe is brought into contact with an inner wall of a peripherally processed hole.

In FIG. 2, the specimen stage is inclined by 45° to have a specimen excision probe 5 contacting with the substrate. The relationship between initial coordinates on an image at a probe tip end and the coordinate information of a probe driving mechanism is beforehand calibrated. When the on-substrate mark 1 is detected by means of image recognition, its positional information is followed to enable the probe to move to a destination point from its initial position. Here, the probe tip end is moved to neighborhood of a center of a front processed hole. Coordinates of the processed hole has been known from processing data and so a probe descent position can be readily calculated by incorporating correction based on tilting of a specimen.

Figure 3:
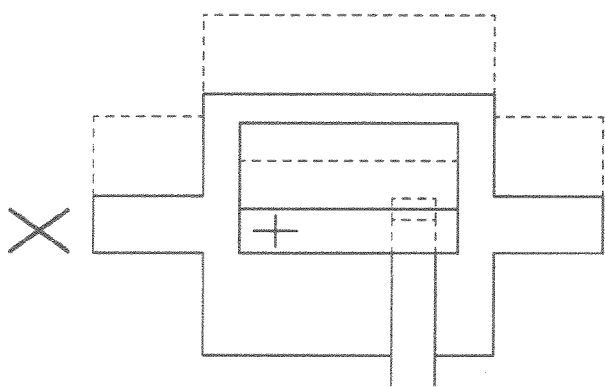
FIG. 3 shows an image observed from above when the probe is brought into contact with the excising specimen part.
Figure 4:
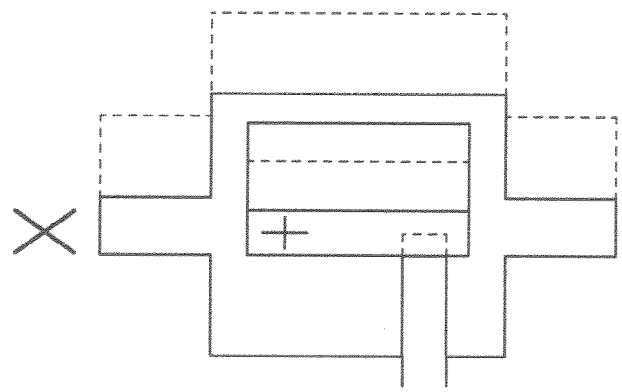
FIG. 4 shows an image observed from above before bonding of the probe.
Figure 9:
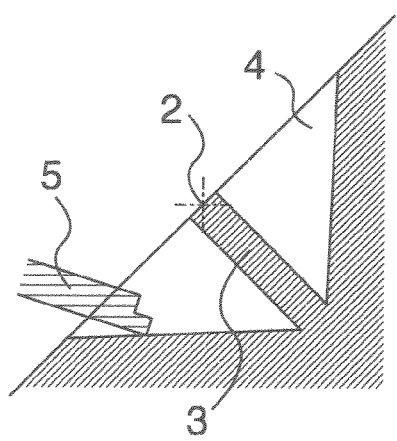
FIG. 9 is a cross sectional view showing a state when the probe is brought into contact with the inner wall of the peripherally processed hole.
Figure 10:
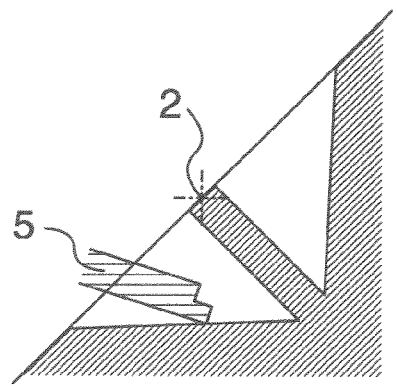
FIG. 10 is a view illustrating process, in which the probe is moved along the inner wall of the peripherally processed hole.
Figure 11:
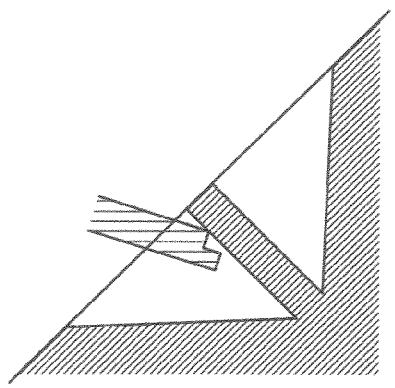
FIG. 11 is a cross sectional view when the probe is brought into contact with the excising specimen part.
Figure 12:
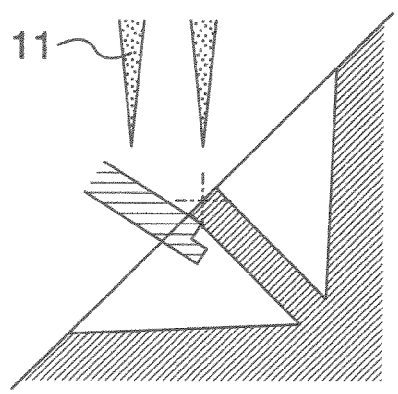
FIG. 12 is a cross sectional view when the probe is being adjusted to an upper end of the excising specimen part.
Figure 13:
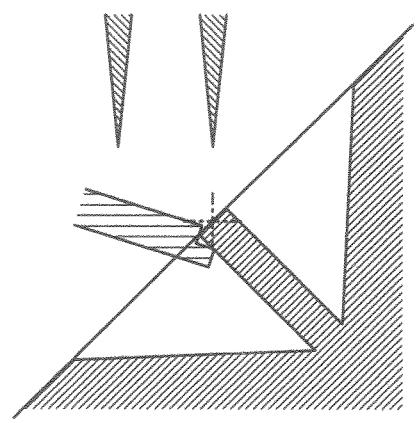
FIG. 13 is a cross sectional view showing a state, in which the probe has been adjusted at the upper end of the excising specimen part.
Figure 14:
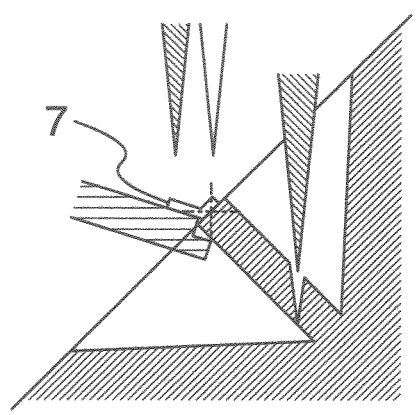
FIG. 14 is a cross sectional view when a deposition film for probe bonding, is formed and the bottom-cutting processing is performed.

Thereafter, the probe is caused to descend vertically and the descent is stopped by detecting contact from a potential change of the probe. In this manner, the probe can be brought into contact with a specimen without breakage of the probe tip end in a state, in which the probe is in side contact with an edge or an inner wall. As shown in FIGS. 2 and 3, the probe is moved about 1.4 times a hole dimension toward the specimen excising part to position the probe tip end in the vicinity of a side wall of the specimen excising part 3. FIGS. 9 and 10 show the positional relationship in a section between the probe and the specimen at this time. Subsequently, when the probe is moved vertically upward as shown in FIG. 11, the probe tip end comes into contact with a thin wall of the excising part since the thin wall is slant. When the probe is moved to an upper part of the thin wall, contact surfaces of the probe and the specimen are generally determined by a stepped shape and a spring property of the probe tip end. FIGS. 4 and 13 show the positional relationship between the specimen and the probe at this time.

Figure 5:
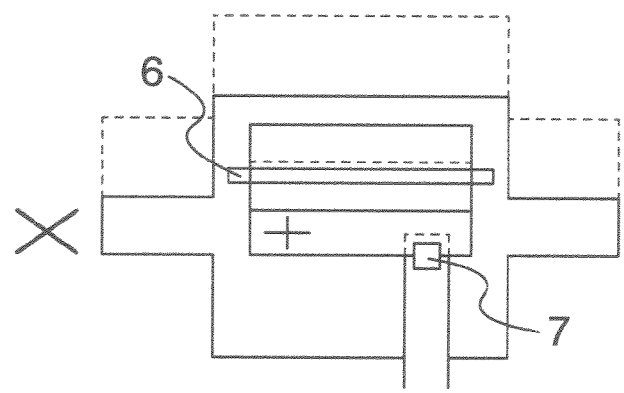
FIG. 5 shows an image observed when the probe is bonded to the excising specimen part and a bottom-cutting pattern is arranged.
Figure 6:
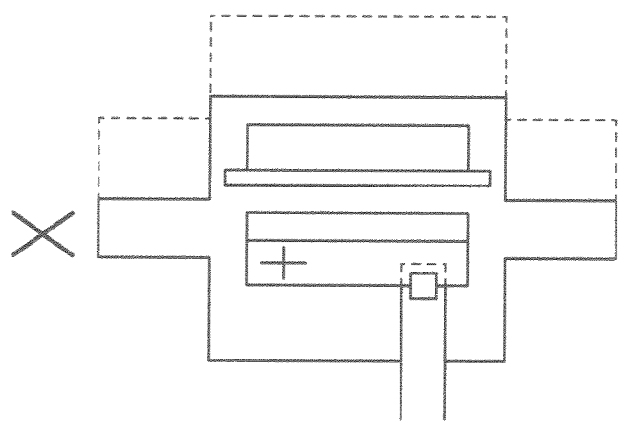
FIG. 6 shows an image observed from above when the excising specimen is excised.

Since a distance between a stepped surface of the probe tip end and the specimen excising part is in the order of 0.5 μm, a nozzle is used to introduce deposition gases to cause a FIB induced deposition around contact surfaces. Thereby, it is possible to readily bond the probe and the specimen as shown in FIG. 5. With a probe having a pointed tip end for general use, deformation of the tip end is liable to cause a change in positional relationship and a contact area is small, so that a margin is small in a bonding process and accurate positioning by an operator is necessary. With the probe of the embodiment, a contact area can be ensured by the above-mentioned procedure of movement and the stepped shape of the probe, so that accurate positioning is made unnecessary. In the bonding process, a tungsten deposition film by the FIB induced deposition is used. A bonding position on an excising specimen at this time may be determined on the basis of either the on-substrate mark 1 or the on-specimen mark 2. However, it is desired that the deposition film is prevented from hanging on the on-specimen mark 2 to make an obstacle to detection of the mark. Relative position of the on-substrate mark 1 and the on-specimen mark 2 in this state gives an origin of displacement measurement for detection of an end point of processing. Since both the on-substrate mark 1 and the on-specimen mark 2 are registered in a state, in which a specimen is kept horizontal, a shape of the specimen when tilted at 45° makes an image, which is contracted cos (45°) times, that is, $1/\sqrt{2}$ times in a vertical direction on the figure. Since comparison with an original image is enabled by means of image processing, there is no obstacle to detection of relative position.

Subsequently, the specimen excising part is separated from a substrate. Coordinates of a processing pattern 6 in this process (bottom cutting) can be determined on the basis of either the on-substrate mark 1 or the on-specimen mark 2. Since a thickness and a width of the specimen excising part are known, the dimension of a processed region can be determined by calculation from coordinates and a dimension of a periphery processing pattern. Since a volume being to be removed by sputtering can be readily calculated, a probe current value of FIB used in processing is used to enable finding an approximation of the processing time when calculation reflects effects of a sputtering rate and a beam incident angle. In the embodiment, since the processing pattern is sized to have a length of 1.5 microns and a breadth of 15 microns and the thin wall of the specimen excising part has a thickness of 3 microns, the volume is 95.5 cubic microns taking account of an inclination of 45°. Since a processed volume per electric charge with an inclination of 45° is known for gallium FIB having an accelerated energy of 30 keV and 0.74 cubic microns/nC, a necessary electric charge is 129 nC. Here, a necessary time on calculation is 172 seconds because of probe current of 0.75 nA.

Figure 7:
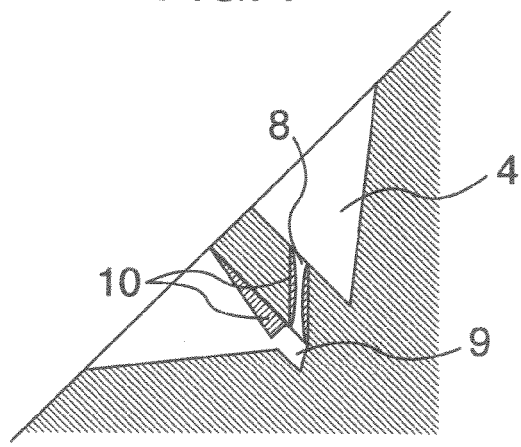
FIG. 7 is a cross sectional view at the time of bottom-cutting processing.

As seen from a sectional shape in FIG. 7, however, a bottom-cut processed hole 8 is close to a bottom of the peripherally processed hole 4 and small in width as compared with a thickness of the specimen excising part, so that slot processing of a high aspect ratio is resulted. With such configuration, a working speed is decreased from the calculation speed since there is caused a phenomenon that a substance subjected to sputtering by ion beams attaches as a re-attaching film 10 to a separated processed part. Accordingly, it is technically difficult to stop ion beams at the end point of processing only by means of control on the beam irradiation time. Conventionally, when manually processed by an operator, whether separation is accomplished is confirmed by recognizing a change in intensity of secondary electrons in the course of processing or temporarily stopping the processing to actually observe an image of secondary electrons.

Figure 8:
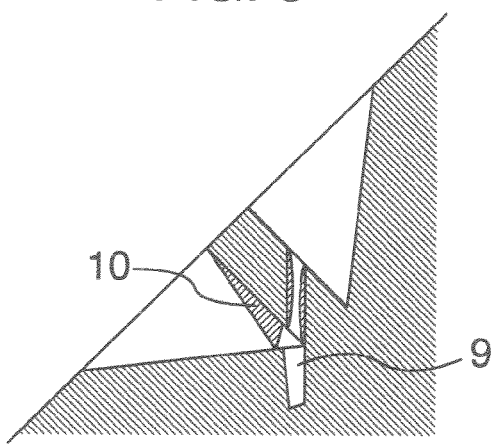
FIG. 8 is a cross sectional view in the case where bonding by a re-attaching film occurs at the time of bottom-cutting processing.

Also, in method of over-etching through setting a processing time longer by 10 to 20% than a calculated time so as to enable sure separation, after a processed hole is formed, a side wall in the vicinity of a hole outlet on a lower side of a specimen is subjected to sputtering, so that re-attachment is brought about not only on an inner wall of the processed hole but also on a rear surface of a specimen excising part on that side, on which the processed hole is formed, and must be again removed. Also, as shown in FIG. 8, there is caused a case where the excising part and a hole inner surface are bonded together by a re-attaching film 10 and cannot be separated from each other. In order to decrease re-attachment in case of a silicon substrate, method of performing a processing while blowing an etching gas including a fluorine compound is effective but in some cases inappropriate for failure analysis of semiconductors because spontaneous etching by gases occurs to subject an observed part to etching. Also, in case of supplying a gas with the use of a nozzle, no effect is frequently produced because the gas is not adequately supplied to a part being shaded by a hole bottom. Accordingly, before a substrate and an excising part are separated by a processing and the problem of bonding by a re-attaching film or the like is caused, it is necessary to surely terminate the processing and stop irradiation of ion beams.

Figure 15:
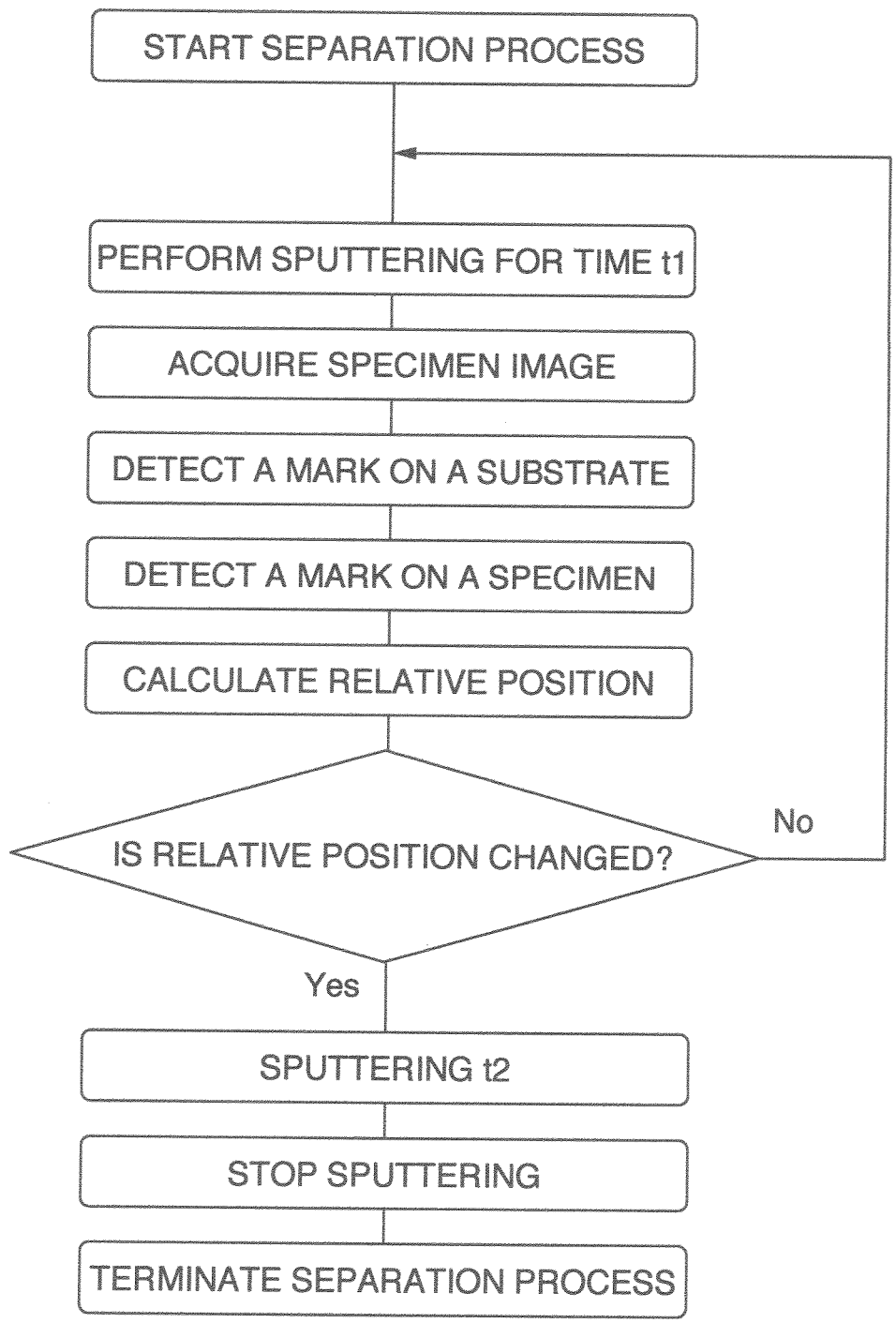
FIG. 15 is a flowchart showing automatic control at the time of the bottom-cutting processing.

In the embodiment, relative position of the on-substrate mark 1 and the on-specimen mark 2 is measured for detection of an end point of the processing for separation of a specimen. While the processing time obtained by calculation of a sputtering rate is 172 seconds as described above, measurement of relative position is performed by extending an ion beam scanning range to a whole region from within a sputtering pattern once in 20 seconds past the lapse of 120 seconds and detecting registered images of the respective marks, which are obtained prior to the start of the processing, among whole images. This procedure is shown in FIG. 15. When an image scanning region is sized to have a length of 50 microns and a breadth of 50 microns and the number of pixels is 512×512 in length and breadth, a pixel is about 0.1 microns in dimension, in which case measurement accuracy in image recognition is around this provided that beams involve no shading.

Figure 16:
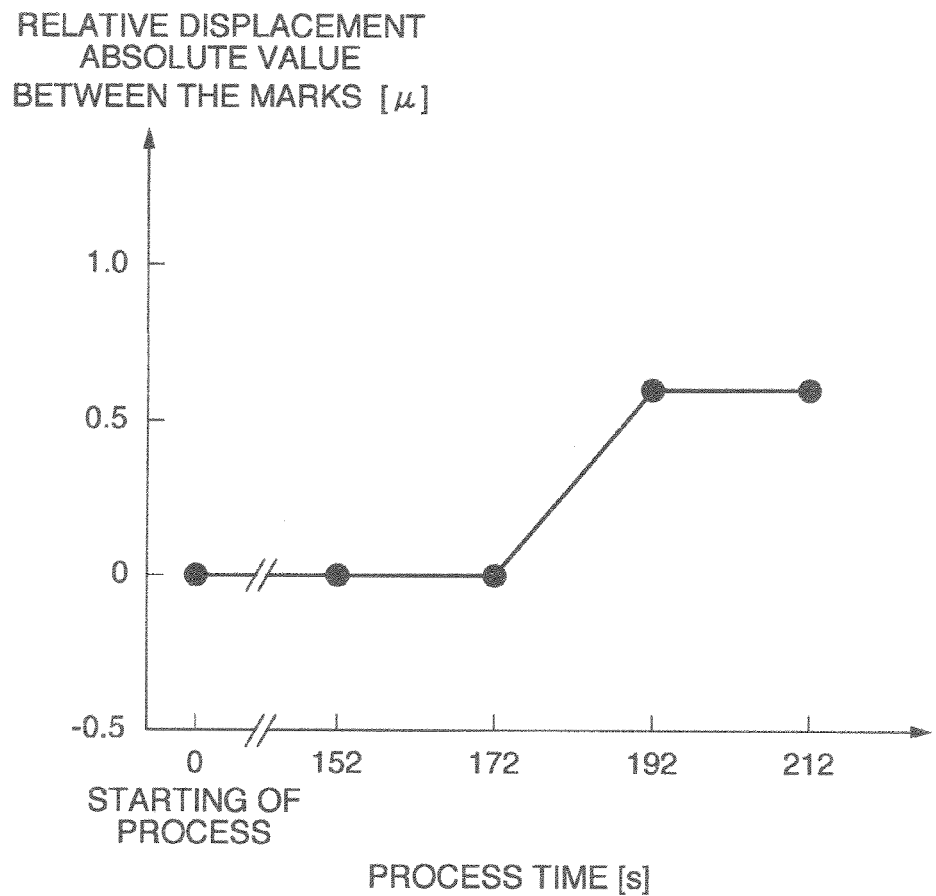
FIG. 16 is a graph showing a change in a distance between the mark on the specimen substrate and the mark on the excising specimen part.

In experiments, a change in relative position between the marks was detected at a point of time amounting to 112% (processing time of 192 seconds) of a processing termination scheduled time. In a measurement after the processing was performed for 20 seconds, an end point of the processing for separation was detected (FIG. 16) because of no positional change and the processing was stopped. The specimen stage was automatically lowered 50 microns to completely separate a substrate and an excising specimen from each other. In order to further reduce formation of a re-attaching film by over-etching, it is favorable to shorten intervals of measurement after observation of displacement to more accurately control over-etching, in which case it is preferred that a mark detection time interval t2 after detection of relative position of the marks in FIG. 15 be shorter than a time interval t1 before detection of positional change.

In the embodiment, a change in the relative position of an excising specimen and a substrate is detected by means of image recognition, an end point of the processing is detected, and the FIB processing is stopped, whereby the processing for separation having a high yield can be performed. Also, by detecting the minute movement of a specimen at an end point of the processing with the use of image recognition, an end point of the processing for separation based on FIB processing can be mechanically detected without relying on a personal judgment. Also, by beforehand forming marks on an excising specimen and a substrate, image recognition of a minute, relative positional movement between the substrate and the excising specimen is improved in accuracy. Also, a probe tip end is stepped in shape whereby the positional relationship between the probe and a specimen is limited. The function of giving a relative, minute displacement to a specimen stage, on which a substrate is put, and a probe prior to the start of the processing, is imparted to a specimen stage moving mechanism and/or a probe position control mechanism whereby a minute specimen movement is magnified and brought about with good repeatability. Also, the function of stopping beam scanning of a FIB device in the course of the processing on the basis of detection of relative position is imparted to the device whereby over-etching since detection of an end point of the processing is prevented.

Embodiment 2

In the present embodiment, separation of a specimen from a substrate with the use of irradiation of focused ion beams and adhesive fixation of an excising specimen to a specimen carrier are automatically performed consistently. Subsequently, an explanation will be given centering on a difference between the present embodiment and Embodiment 1.

Figure 17:
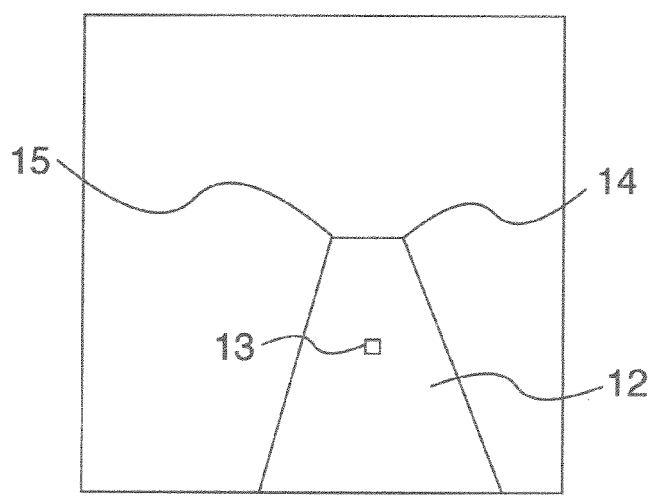
FIG. 17 shows an image observed in a position, in which a marked stepped probe is registered.
Figure 18:
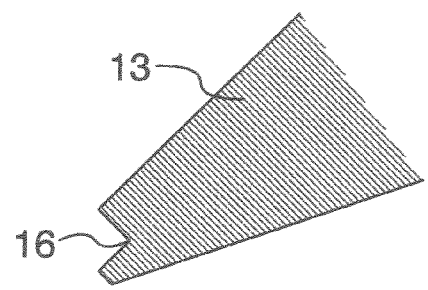
FIG. 18 shows a cross sectional shape of the marked stepped probe.

In the embodiment, any mark is not processed on an excising specimen but a mark on a probe is detected and separation from a substrate is detected. FIG. 17 shows a probe 12 with a mark used in the embodiment. The marked probe 12 is formed on an upper surface thereof with an on-probe mark 13. FIG. 18 shows a sectional shape of the probe. A step is formed at a tip end and the probe comes into contact with a specimen not at a point but on a line segment along the specimen, so that a margin in a bonding process is large.

In order to exercise a positional control of the probe tip end, an operator manually performs registration of a probe initial position. Relative positional relationships among the on-probe mark 13 and probe tip ends 14, 15 are registered on an image in FIG. 17. At the time of registration, the probe tip end is beforehand adjusted to be substantially the same in level as a specimen surface. Such registration is performed by first preparing a specimen mount, which serves as a reference, separately from a specimen, finding an eucentric level, which is not varied in level at the time of inclination and serves as a level reference, and then confirming contact between the reference specimen mount and the probe by means of an image of FIB secondary electrons. This is decided as a reference level of the probe.

Subsequently, the probe is moved, respectively, in X-direction and Y-direction of a probe driving mechanism and the position of the on-probe mark is detected likewise. This operation enables calculating the transformation relationship between coordinates of the probe driving mechanism and pixel coordinates on a screen. A central position of a FIB scanned image and an origin position of the probe driving mechanism do not usually agree with each other but they are turned in some cases. Also, a display multiplying factor on the screen is not accurate. Therefore, in case of driving the probe with the FIB scanned image as a reference, the initial calibration is performed to find a transformation formula (generally, a linear expression) of pixel coordinates of an image and coordinates of the driving mechanism.

A periphery processing is performed at a plurality of points on a substrate, in which case a periphery processing pattern is arranged with an on-substrate mark as a reference. Therefore, peripherally processed shapes at all processing points are registered in a control device. Since respective points on a specimen surface are varied in level due to inclination and warp of a specimen to generate dispersion in relative distance between them and the probe, a specimen stage is adjusted in level at respective processing points and coordinates are registered in the control device. For the level of the stage, movement is made so as to cancel a travel due to inclination, that is, a so-called an eucentric adjustment is made, but the use of a FIB observed image having a small depth of focus enables substitution by focusing effected by stage movement.

Figure 19:
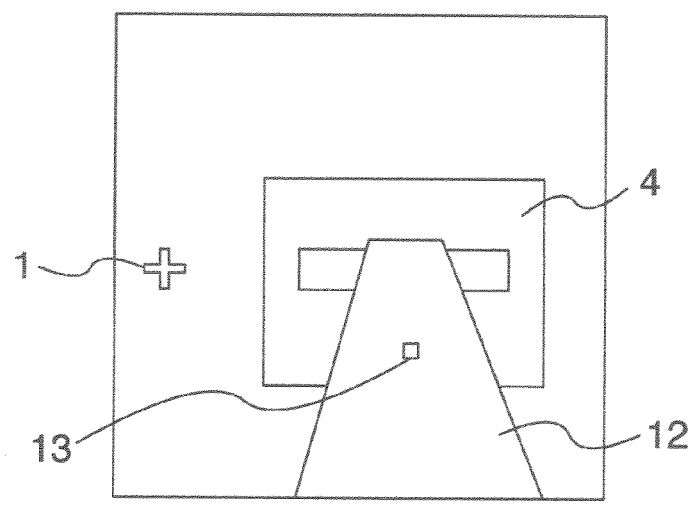
FIG. 19 is a plan view when the marked stepped probe is introduced onto a first point for excision.

FIG. 19 shows an image of secondary electrons when the specimen stage is moved to registered coordinates of a first processing point in a state, in which the probe is retreated, after the on-substrate mark 1 is detected, the stage level is lowered by 30 microns, and thereafter the probe is inserted to give a reference level. Since the specimen stage and the probe driving mechanism as used are ±2 millimeters in level repeatability, the specimen and the probe will not strike against each other in this operation.

Since the on-probe mark 13 can be detected from a FIB scanned image in FIG. 19, pixel coordinates of the probe tip end in the screen can be found from registered data of points at the probe tip end, that is, 14, 15 in the FIB scanned image in FIG. 17. Therefore, since positions of a thin wall being an excising specimen and the peripherally processed hole are found from coordinates of the on-substrate mark 1 and processing pattern data of the periphery processing registered at the point, coordinates of the driving mechanism are set in a manner to position the probe tip end at a center of a front hole of the periphery processing in the same manner as in Embodiment 1. At this time, that transformation formula of pixel coordinates and coordinates of the probe driving mechanism, which is beforehand found, is used. Since the on-substrate mark 1 and the on-probe mark 13 are substantially the same in level, a focus voltage of an objective lens having performed acquisition and detection of an image is the same for the both, so that an image undergoes no positional shift due to an alignment error of an optical system. In experiments, when the probe driving mechanism had the XY accuracy of ±0.2

μm, the probe tip end could be moved to a peripherally processed hole of a processed specimen.

Subsequently, the probe is brought into contact with the substrate. In this process, detection of a position of the on-probe mark 13 with the FIB scanned image and a motion of lifting the stage in a pitch of 2 microns are alternately performed. Since the position of the on-probe mark 13 changes due to contact between the substrate and the probe, the contact is detected by detection of displacement and the motion is stopped. When vibrations generated from a drive motor cause the probe to vibrate, contact is erroneously detected in some cases in the course of stage movement in spite of no contact, so that after minute movement of the stage, a waiting time of several seconds is taken and the mark on the probe is detected. After detection of contact, the level of the specimen is moved to coordinates in a step forward prior to the contact, it is confirmed that the on-probe mark 13 is returned to the initial position, and the motion is terminated.

When being contacted by the probe, a specimen image is frequently varied in contrast due to a change in electric potential but the on-probe mark 13 as detected is not varied much in contrast. While detection, as usually used, of contact by a change in electric potential is usable, there is an advantage that the method of detection of displacement is usable in the case where a substrate surface is insulating.

Since the bonding process is liable to be decreased in success rate when the positional relationship of the probe tip end and the specimen excising part is not determined, contact between the probe and the specimen excising part is performed in the following procedure in order to make the positional relationship of the probe and the specimen substantially constant and to increase a contact region.

Figure 20:
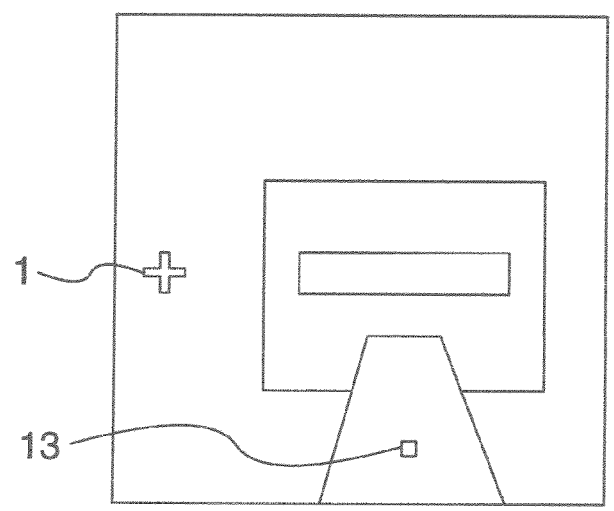
FIG. 20 is a plan view when the marked stepped probe is moved to above the peripherally processed hole above a point of excision.
Figure 21:
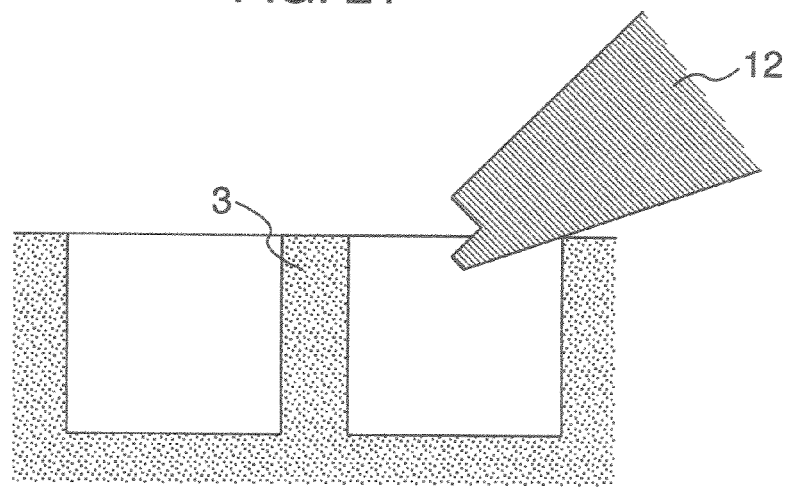
FIG. 21 is a cross sectional view when the marked stepped probe is brought into contact with the substrate.
Figure 22:
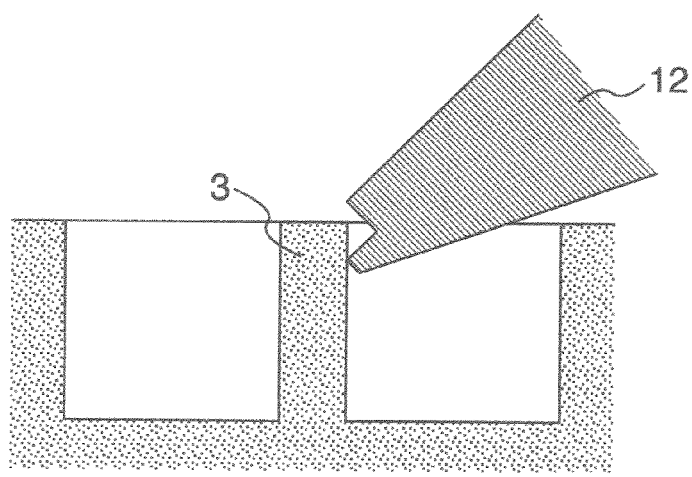
FIG. 22 is a cross sectional view when a stage is moved to bring a tip end of the marked stepped probe into contact with the excising specimen part.
Figure 23:
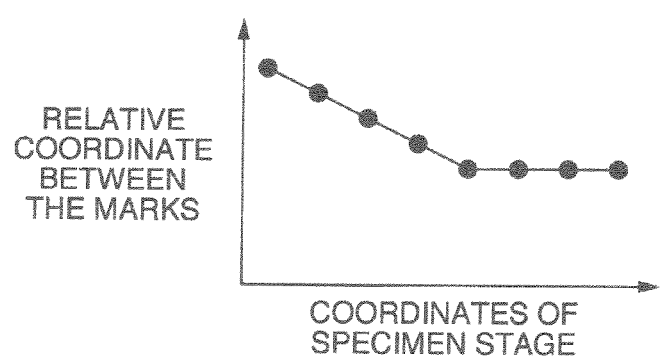
FIG. 23 is a plan view when the stage is moved to bring the tip end of the marked stepped probe into contact with the excising specimen part.
Figure 24:
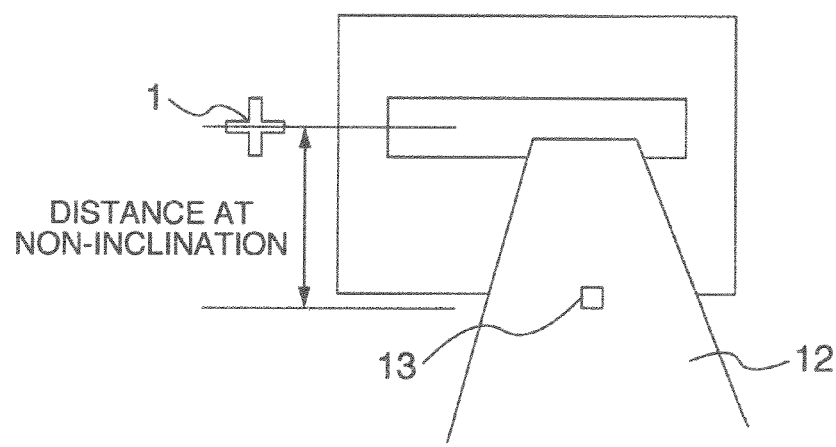
FIG. 24 is a graph showing the relationship of relative distances among a Y-coordinate of a specimen stage, the mark on the excising specimen, and the mark on the specimen substrate.

First, initial positions of the on-substrate mark 1 and the on-probe mark 13 are detected (FIG. 20). Since the substrate and the probe are in contact with each other and the substrate surface comes to a substantially eucentric level, there are little influences of focus misalignment. Subsequently, while the specimen stage is reciprocated by a distance of 0.5 microns in an up and down direction in FIG. 20, that is, in an axial direction of the probe, it is moved downward in a step of 0.5 microns to gradually approach the specimen excising part. FIG. 21 and FIG. 22 show the positional relationship of the probe 12 and the specimen excising part 13 as viewed in a direction along a section. Ion beams are scanned on the mark in conformity to a period of reciprocation, an image is taken, and relative position of the on-substrate mark 1 and the on-probe mark 13 is measured. At this time, since the probe occasionally comes into contact with an edge of the peripherally processed hole, the probe is occasionally moved following the movement of the specimen but is returned to the same position owing to a spring property upon reciprocation. When the excising specimen and the probe tip end come into contact with each other, however, relative position thereof is made constant. FIG. 23 shows changes in relative coordinates and FIG. 24 shows the positional relationship of the probe 12 and the specimen. Since the position of the tip end of the probe 12 is initially calibrated relative to the on-probe mark 13, the probe can be brought into direct contact with the specimen excising part but doing in the procedure described above is high in success rate because the periphery processing is not occasionally performed in accordance with the pattern. In the case where the positional relationship of the marks at the time of contact is much different from a design value in a state shown in FIG. 24, the process of contact is redone from the beginning or excision of the specimen is given up as an error, in which foreign matters attach to the probe to result in poor contact, and movement to a subsequent processing point is made.

Figure 25:
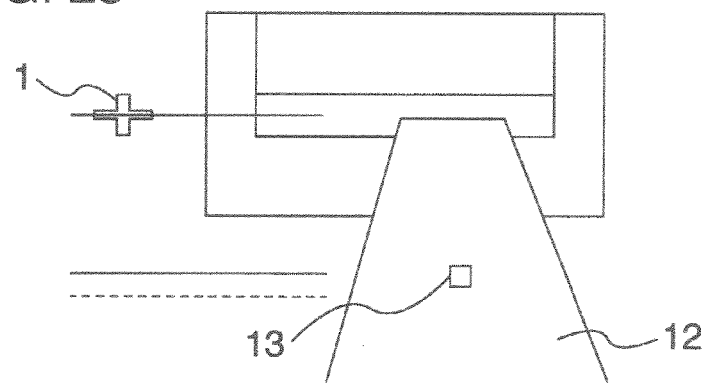
FIG. 25 shows an image observed when the specimen stage is eucentrically inclined by 45° in a state of contact.
Figure 26:
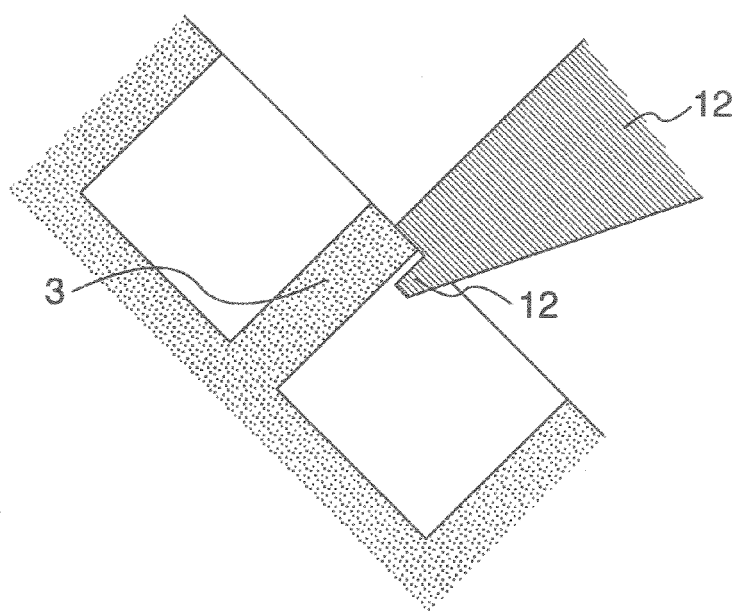
FIG. 26 is a cross sectional view when the specimen stage is eucentrically inclined by 45° in the state of contact.

Finally, the stage is urged into eucentric inclination to an angle of inclination of 45°. This operation causes the specimen excising part to be inscribed not in a topmost end of the probe but in the stepped portion 16 at the probe tip end. FIG. 25 shows this state and FIG. 26 shows a section thereof.

Figure 27:
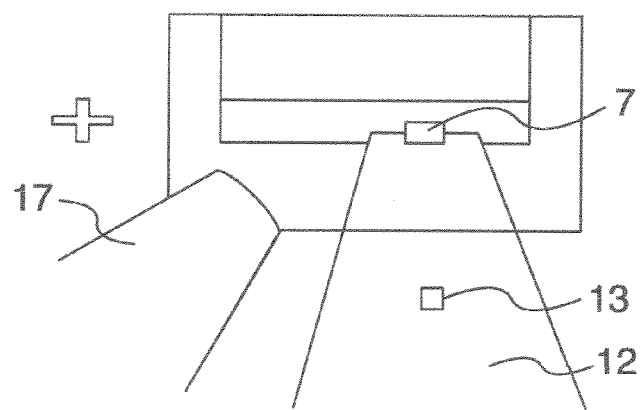
FIG. 27 is a view illustrating the positional relationship among the specimen, the probe, and a gas nozzle when the deposition film for probe bonding, is formed.

Subsequently, the probe and the excising specimen are bonded together as shown in FIG. 27. At this time, while a probe bonding deposition film 7 is arranged with the on-probe mark 13 as a reference, the probe 12 is somewhat changed in angle from that at the time of registration in FIG. 17 due to contact with the specimen and so a slight error is involved in a vertical direction. Therefore, the pattern is magnified about two times in the vertical direction to accommodate such error.

Figure 28:
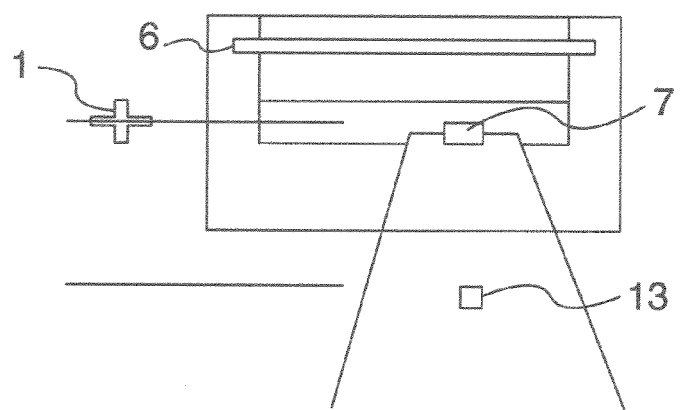
FIG. 28 shows an image observed when the deposition film for probe bonding, is formed and the bottom-cutting processing is performed.
Figure 29:
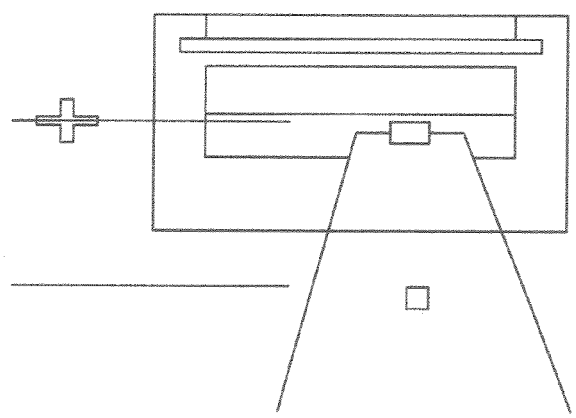
FIG. 29 shows an image observed when termination of the bottom-cutting processing is detected.

FIGS. 28 and 29 show a process of separating the excising specimen from the substrate. Like Embodiment 1, the excising specimen is excised from the substrate by irradiating FIB in the bottom-cutting processing pattern 6 while monitoring relative position of the on-substrate mark 1 and the on-probe mark 13 every specified period of time, and performing the bottom-cutting processing. In this process, when the probe 12 is close toward the substrate, a distance between the specimen and the substrate at the time of processing is unlikely to be existed. Therefore, when the probe is moved downward in the screen, or an angle of inclination of the specimen is decreased about 0.5 to 1° after bonding, detection of the bottom-cutting processing becomes high in success rate. In experiments, the latter was adopted, the angle of inclination was restored 0.5° after termination of the bonding process to be made 44.5°, and the processing for separation was performed. Relative position of the marks was monitored every 10 seconds since the lapse of 180 seconds amounting to 90% of a processing time as calculated, monitoring at intervals of 5 seconds was performed after detection of displacement, and after the displacement became constant after the lapse of 215 seconds, the processing was stopped determining that the processing for separation was terminated.

When plural processing are performed successively, a peripherally processed hole is formed not to be sized in a manner as designed because of an internal structure of a substrate and a fine change in processing beam current, so that the processing for separation does not succeed in some cases. In case of excision at a plurality of specimen points, an unprocessed specimen is left when the processing is stopped in the course. Therefore, assuming in experiments that 150% of a processing time as calculated was made an upper limit, fail was determined in the case where detection of separation on a change in relative position did not function in the meantime. At this time, an excising specimen and a probe were separated from each other by irradiating ion beams on a probe bonding deposition film 7 used in bonding of the probe and the specimen. Thereafter, the processing of an associated processing point is stopped and the procedure is moved to a subsequent processing point. In terms of control software, an error is displayed so that an operator can know the fail. Except this, an error processing for abnormality in a device, such as a change in emission current from an ion source, is performed in a usual manner.

After a relative displacement between the marks can be detected and the processing for separation is completed, the procedure proceeds to a process of fixing the excising specimen to a specimen carrier. After the probe, to which the excising specimen is once bonded, is caused to retreat to a position higher 50 microns than an eucentric level and a stage, on which the substrate is mounted, is also caused to retreat, a separate stage, on which the specimen carrier for fixation of the excising specimen is mounted, is inserted and moved to an eucentric position. Here, the specimen carrier comprises a convex-shaped mesh for transmission electron microscopes. It does not matter whether the specimen carrier is mounted on the same stage as that, on which the specimen is mounted. However, a fixed position is beforehand determined, coordinates are registered, a mark for matching is formed, and an eucentric adjustment is made.

Figure 30:
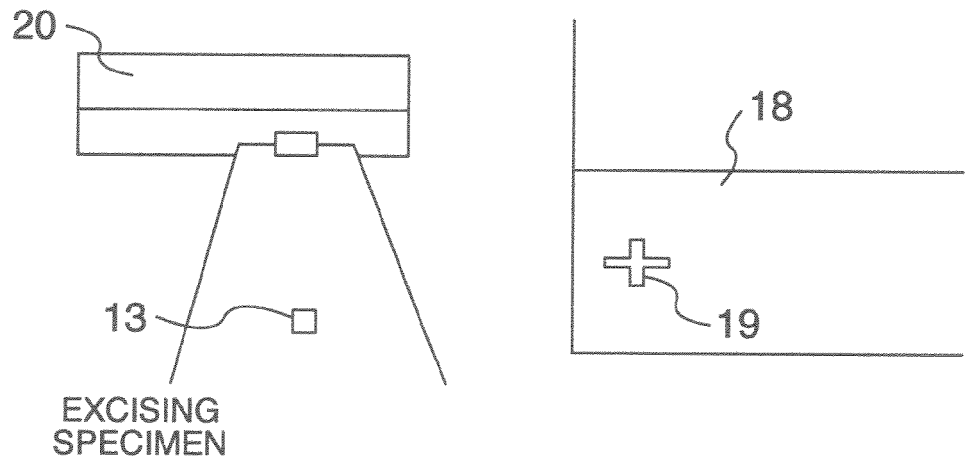
FIG. 30 shows an image observed when a specimen carrier is moved to neighborhood of the excising specimen and the probe.
Figure 31:
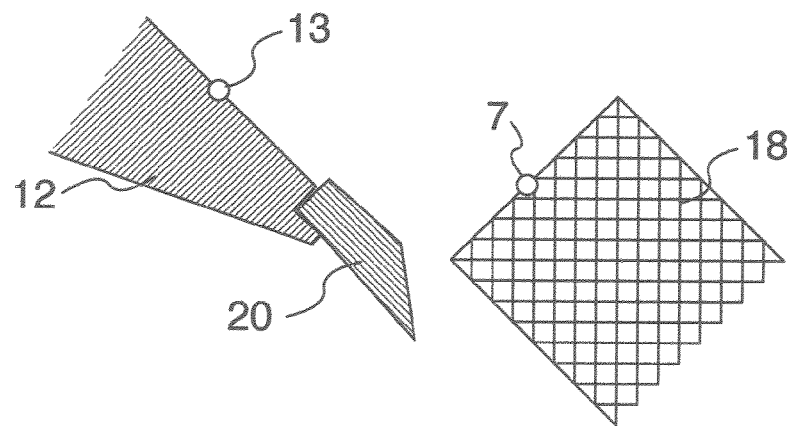
FIG. 31 is a cross sectional view illustrating the positional relationship among the excising specimen, the probe, and the specimen carrier.
Figure 32:
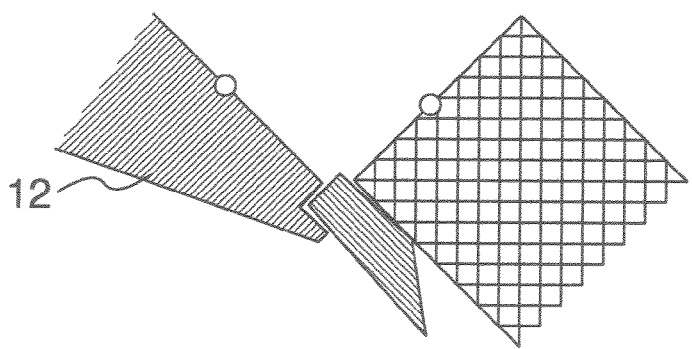
FIG. 32 is a cross sectional view illustrating the positional relationship when the excising specimen is bonded to the specimen carrier.
Figure 33:
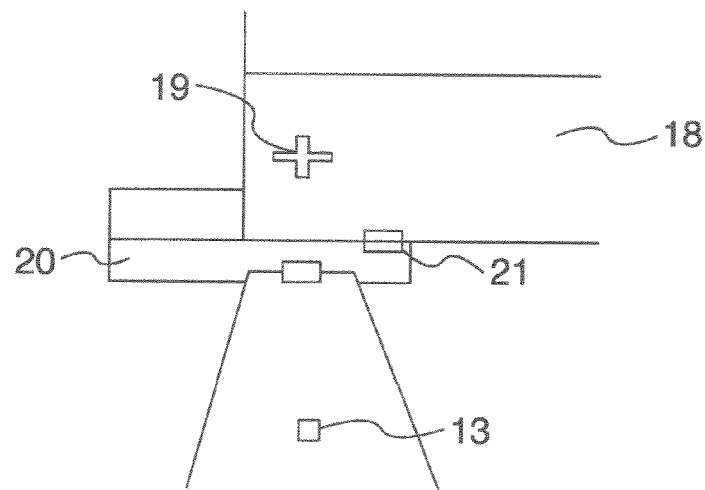
FIG. 33 shows an image observed to show the positional relationship when a deposition film pattern for carrier fixation of the excising specimen is arranged.

As shown in FIG. 30, the probe 12 is returned to the reference level and the specimen carrier 18 is urged into eucentric inclination at 45° in the same direction as the excising specimen 20. An on-carrier mark 19 is beforehand prepared on the specimen carrier 18 in a position of a particular distance from an edge, and a mark image is registered and detected. In an initial state, since the specimen carrier is also disposed in the reference level owing to eucentric adjustment, a difference in level between the excising specimen and the carrier is approximately the sum of the level of the excising specimen 20 and a mechanical error of ±2 microns as shown in FIG. 31. In order to avoid falling-off and breakage of an excising specimen due to collision, the excising specimen 20 is fixed to not an upper end but a side of the specimen carrier.

Since a distance between the excising specimen 20 and the specimen carrier side can be calculated from pattern data of the peripherally processed hole, the on-probe mark 13, and the on-carrier mark 19, final coordinates of the probe driving mechanism in a fixed position or the specimen carrier stage mechanism are calculated and set. Here, it is important to make the excising specimen slightly higher than an upper surface of the specimen carrier. If not so, FIB cannot be irradiated on bonded portions of the specimen carrier and the excising specimen, so that a weak adhesive strength results. Finally, the probe bonding deposition film 7 used in bonding of the probe is removed by FIB sputtering to achieve separation of the probe and the excising specimen. A probe tip end and the excising specimen may be cut by means of FIB sputtering to achieve separation of the probe and the excised specimen.

Figure 34:
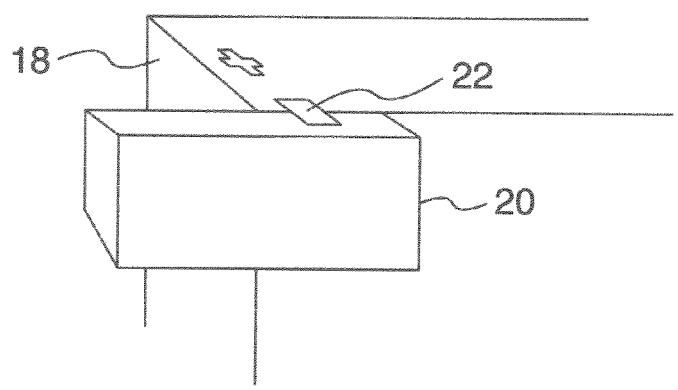
FIG. 34 shows a configuration after the excising specimen is bonded to the specimen carrier.
Figure 35:
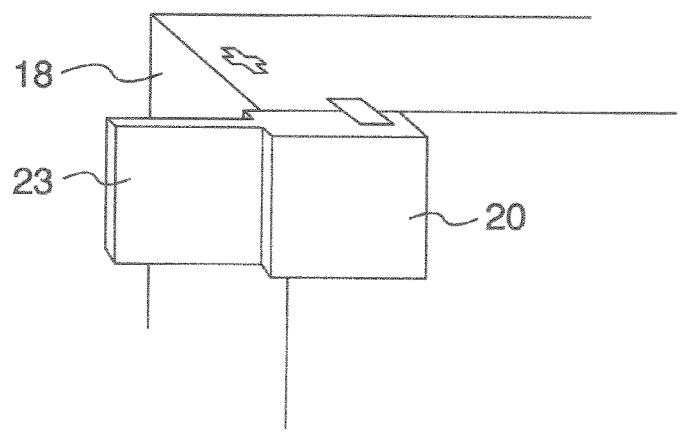
FIG. 35 shows a configuration in the course of forming a thin film from the excising specimen on the specimen carrier.

Also, in this process, in the case where troubles such as incapability of detection of the position of the specimen carrier are caused, the process is stopped. Since the specimen has already been bonded to the probe, bonding is made on another fixed point on the carrier, which point is registered. FIG. 34 shows a shape of the excising specimen after bonding and FIG. 35 shows a specimen shape in a processing of making a thin film. As seen from FIG. 35, what can be made a thin film and observed with a transmission electron microscope is only that portion, which does not overlap the specimen carrier. While an observation enabling range is widened by locating the fixed position at an end of the excising specimen, it is desired that the fixed position overlap the specimen carrier by several microns in view of a yield in an automatic process.

After the excising specimen is fixed to the specimen carrier, the specimen carrier is retreated. Before the stage on which the substrate is mounted is introduced and moved to a second processing point, an unnecessary probe bonding deposition film attached to the probe is removed by means of sputtering.

In addition, while the on-probe mark 13 is used as a reference in the embodiment, an on-specimen mark 2 may be used instead.

Embodiment 3

While the degree of freedom of motion of the probe is in three directions, that is, X, Y, Z directions in the two previous embodiments, a rotary probe having the rotational degree of freedom about an axis of the probe is used in the present embodiment. Subsequently, an explanation will be given centering on a difference between the present embodiment and Embodiments 1 and 2.

Figure 36:
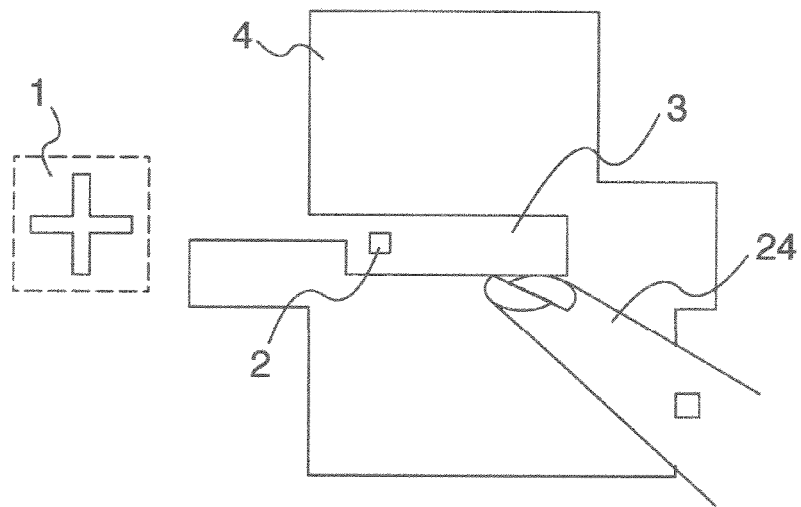
FIG. 36 is a plan view when a rotary probe is brought into contact with the excising specimen part.

FIG. 36 shows a state, in which a tip end of a rotary probe 24 is brought into contact with an excising specimen, of which the periphery processing is terminated, like said embodiments. In the same process as that in Embodiment 2, the tip end of the rotary probe is calibrated relative to the on-probe mark 13 by means of manual operation. Contact between the probe and the substrate is detected by alternately performing upward step movement of the specimen stage and monitoring of the position of the on-probe mark 13. Since the probe is inserted from rightward under, this specimen is beforehand made fairly wide on a rightward lower side, which is subjected to periphery processing, so that there is no interference between the rotary probe 24 and the peripherally processed hole 4. Also, this specimen has already been subjected to automatic bottom-cutting processing to be in the form of a cantilever beam. Therefore, without inclining the stage, the processing for separation is enabled by subjecting that portion at a left end of the specimen excising part 3, which is connected to the substrate, to sputtering.

Figure 37:
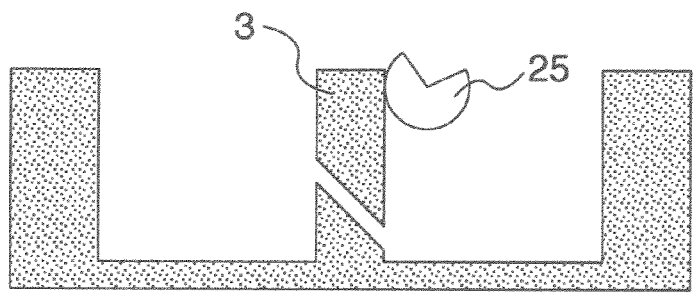
FIG. 37 is a cross sectional view when the rotary probe is brought into contact with the excising specimen part.
Figure 38:
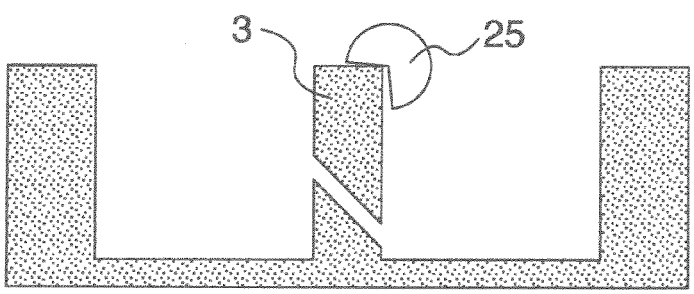
FIG. 38 is a cross sectional view when the rotary probe is rotated to be brought into contact with an upper part of the specimen.
Figure 39:
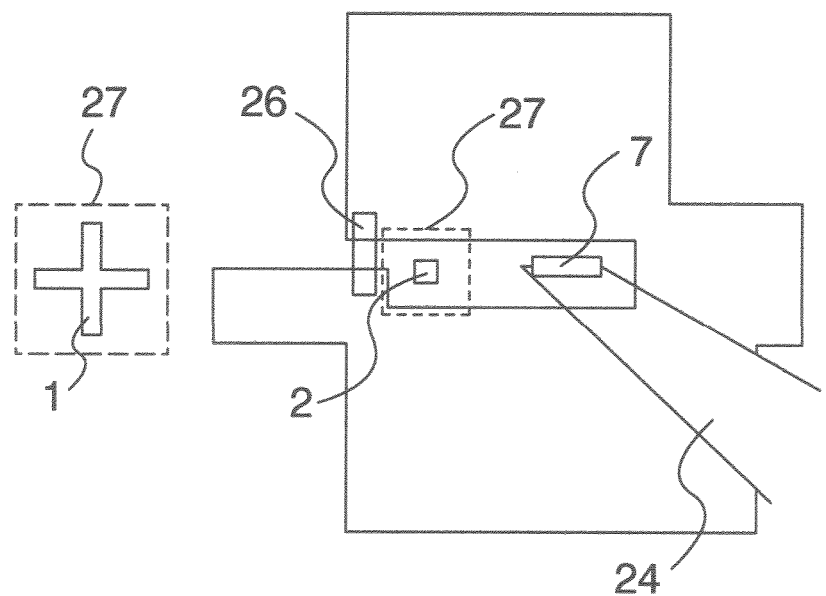
FIG. 39 shows a plane image when the rotary probe is rotated to be brought into contact with and bonded to the upper part of the specimen.
Figure 40:
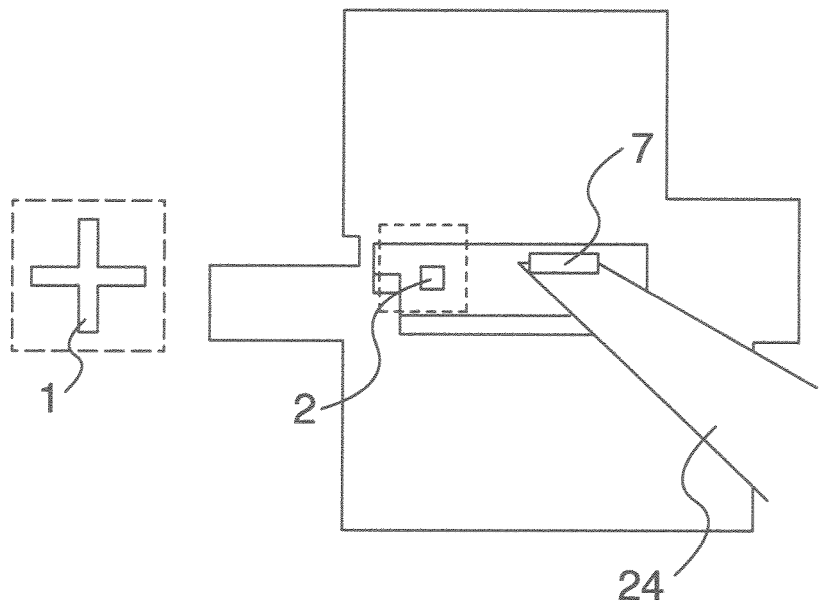
FIG. 40 shows plane images of the specimen and the probe when termination of a processing for separation is detected based on displacement of image.

Like the probes in Embodiment 1 and Embodiment 2, the rotary probe is provided at the tip end thereof with a stepped shape, which corresponds to a convex portion of the specimen, and the stepped shape includes a surface being slant to an axis of rotation of the probe and is rotated like a drill bit to catch the specimen. FIGS. 37 and 38 show this process of motion. A conical surface serves as a first contacting surface, rotation orients the stepped shape toward the specimen, and since the probe is forced against the specimen, rotation through about 180 degrees causes the stepped portion of the probe to catch a corner on an upper surface of the specimen to make rotation hard. At this time, the upper surface and the stepped surface of the probe are in closely contact with each other to enable creating a stable positional relationship in the same manner as the stepped probe described above. In this state, a probe bonding deposition film 7 is formed to fix the rotary probe and the specimen excising part together as shown in FIG. 39. Further, a substrate separation processing pattern 26 is arranged to accomplish the processing. At this time, the processing is performed while measuring the relationship between the on-substrate mark 1 and the on-specimen mark 2 in the same manner as in the embodiments described above. A rectangle 27 shown by broken lines in FIG. 39 is within a FIB scanning range at the time of measurement of mark positions and corresponds to a region, in which FIB is partially scanned in the processing to monitor the mark positions. Since stress generated by rotation of the probe causes the mark 2 to move at the same time as termination of separation, this movement is detected to stop the processing for separation. Thereafter, the processes of excision of the specimen and fixation to the specimen carrier are the same as in the embodiments described above.

INDUSTRIAL APPLICABILITY

Unmanned preparation of a minute specimen becomes possible and time in operating conditions of a device can be extended sharply. Also, it is possible to increase the number of specimens for failure analysis of semiconductor devices to efficiently improve the semiconductor devices in yield and perform production control.

REFERENCE SIGN LIST

1: on-substrate mark
2: on-specimen mark

3: specimen excising part
4: peripherally processed hole
5, 105: probe
6: bottom-cutting processing pattern
7: probe bonding deposition film
8: bottom-cut processed hole
9: processed slot on a lower side of a thin wall
10: re-attaching film
11: FIB
12: probe with a mark
13: on-probe mark
14, 15: probe tip end point
16: probe tip end stepped portion
17: gas nozzle
18: specimen carrier
19: on-carrier mark
20: excising specimen
21: deposition film processing pattern for carrier fixation
22: deposition film for carrier fixation
23: thin wall portion
24: rotary probe
25: rotary probe tip end
26: substrate separation processing pattern
27: FIB scanning range at the time of mark position measurement
100: charged particle beam device
101: ion beam column
102: electron beam column
103: vacuum specimen chamber
104: specimen stage
106: probe driving unit
108: detector
109: display
110: arithmetic processing unit
111: specimen
112: nozzle tip end
115: deposition gas source
121: ion beam control means
122: electron beam control means
123: detector control means
124: stage control means
125: deposition gas source control means
126: probe control means

The invention claimed is:

1. A specimen preparation device comprising:
a specimen stage on which a specimen is mounted;
an ion beam optical system configured irradiate an ion beam;
transfer means for transferring an excising specimen separated from the specimen by means of ion beam irradiation; and
an arithmetic unit configured to control the ion beam optical system,
wherein the device is structured such that when an ion beam is irradiated on the specimen to separate the excising specimen from the specimen, a mark formed in a region, which makes the excising specimen, on the specimen and a mark formed in another region other than said region are measured and the ion beam irradiation is stopped in the case where a relative position between the marks is put in a predetermined condition.

2. A specimen preparation device comprising:
a specimen stage on which a specimen is mounted;
an ion beam optical system configured to irradiate an ion beam;
transfer means for transferring an excising specimen separated from the specimen by means of ion beam irradiation; and
an arithmetic unit configured to control the ion beam optical system,
wherein the device is structured such that when an ion beam is irradiated on the specimen to separate the excising specimen from the specimen, a mark formed on the transfer means holding a region, which makes the excising specimen, on the specimen and a mark formed in another region other than said region, which makes the excising specimen, on the specimen are measured and the ion beam irradiation is stopped in the case where a relative position between the marks is put in a predetermined condition.

3. A specimen preparation device comprising:
a specimen stage on which a specimen is mounted;
an ion beam optical system configured to irradiate an ion beam;
transfer means for transferring an excising specimen separated from the specimen by means of ion beam irradiation; and
an arithmetic unit configured to control the ion beam optical system,
wherein the device is structured such that when the transfer means is moved and brought into contact with the excising specimen, a mark formed on the transfer means and a mark formed in a region, which makes the excising specimen, on the specimen are measured and the transfer means is stopped in the case where a relative position between the marks is put in a predetermined condition.

4. A specimen preparation device comprising:
a specimen stage on which a specimen is mounted;
an ion beam optical system configured to irradiate an ion beam;
transfer means for transferring an excising specimen separated from the specimen by means of ion beam irradiation; and
an arithmetic unit configured to control the ion beam optical system,
wherein the device is structured such that when the transfer means is moved and brought into contact with the excising specimen, a mark formed on the transfer means and a mark formed in a region other than another region, which makes the excising specimen, on the specimen are measured and the transfer means is stopped in the case where a relative position between the marks is put in a predetermined condition.

5. A specimen preparation device comprising:
a specimen stage on which a specimen is mounted;
an ion beam optical system configured to irradiate an ion beam;
transfer means for transferring an excising specimen separated from the specimen by means of ion beam irradiation;
a specimen holder configured to hold the excising specimen; and
an arithmetic unit configured to control the ion beam optical system,
wherein the device is structured such that when the excising specimen held on the transfer means is transferred to the specimen holder, a mark formed on the excising specimen and a mark formed on the specimen holder are measured and movement of the transfer means is stopped in the case where a relative position between the marks is put in a predetermined condition.

6. A specimen preparation device comprising:
a specimen stage on which a specimen is mounted;
an ion beam optical system configured to irradiate an ion beam;
transfer means for transferring an excising specimen separated from the specimen by means of ion beam irradiation;
a specimen holder configured to hold the excising specimen; and
an arithmetic unit configured to control the ion beam optical system;
wherein the device is structured such that when the excising specimen held on the transfer means is transferred to the specimen holder, a mark formed on the transfer means for transfer of the excising specimen and a mark formed on the specimen holder are measured and movement of the transfer means is stopped in the case where a relative position between the marks is put in a predetermined condition.

7. The specimen preparation device according to claim 1, further comprising an electron beam column configured to irradiate an electron beam, and wherein the marks are measured by the electron beam.

8. The specimen preparation device according to claim 1, wherein an ion beam condition in measuring the marks can be changed to an ion beam condition in processing a specimen.

9. The specimen preparation device according to claim 1, wherein the ion beam comprises a focused ion beam.

10. The specimen preparation device according to claim 1, wherein the ion beam comprises a projection-type ion beam.

11. The specimen preparation device according to claim 1, wherein the transfer means comprises a probe.

12. The specimen preparation device according to claim 11, wherein the probe is provided with a step at a region which comes into contact with the excising specimen.

13. The specimen preparation device according to claim 11, wherein the probe includes at a tip end thereof two or more steps aligned in an axial direction of the probe.

14. The specimen preparation device according to claim 11, wherein the probe includes at a tip end thereof at least two or more steps aligned in a direction substantially perpendicular to an axis of the probe.

15. The specimen preparation device according to claim 1, wherein the transfer means comprises a micro manipulator.

16. The specimen preparation device according to claim 1, wherein the specimen stage and/or the transfer means are/is finely driven so that pressure is generated between the excising specimen and the transfer means.

17. The specimen preparation device according to claim 1, wherein relative parallel movement and/or relative inclined movement of the specimen stage and the transfer means are/is made so that pressure is generated between the excising specimen and the transfer means.

18. The specimen preparation device according to claim 11, wherein the probe is rotated about an axis of the probe so that pressure is generated between the excising specimen and the probe.

19. The specimen preparation device according to claim 1, wherein an ion beam is irradiated on the specimen to prepare a mark formed in a region, which makes the excising specimen, on the specimen and/or a mark formed in another region other than said region, which makes the excising specimen, on the specimen.

20. A control method for a specimen preparation device, the method comprising steps of: mounting a specimen on a specimen stage; irradiating an ion beam by way of an ion beam optical system; transferring by way of transferring means, an excising specimen separated from the specimen by means of ion beam irradiation; and controlling the ion beam optical system with an arithmetic unit,
wherein when an ion beam is irradiated on the specimen to separate the excising specimen from the specimen, a mark formed in a region, which makes the excising specimen, on the specimen and a mark formed in another region other than said region are measured and the ion beam irradiation is stopped in the case where a relative position between the marks is put in a predetermined condition.

21. A control method for a specimen preparation device, the method comprising steps of: mounting a specimen on a specimen stage; irradiating an ion beam by way of an ion beam optical system; transferring by way of transferring means, an excising specimen separated from the specimen by means of ion beam irradiation; and controlling the ion beam optical system with an arithmetic unit,
wherein when an ion beam is irradiated on the specimen to separate the excising specimen from the specimen, a mark formed on the transfer means holding a region, which makes the excising specimen, on the specimen and a mark formed in another region other than said region, which makes the excising specimen, on the specimen are measured and the ion beam irradiation is stopped in the case where a relative position between the marks is put in a predetermined condition.

22. A control method for a specimen preparation device, the method comprising steps of: mounting a specimen on a specimen stage; irradiating an ion beam by way of an ion beam optical system; transferring by way of transferring means, an excising specimen separated from the specimen by means of ion beam irradiation; and controlling the ion beam optical system with an arithmetic unit,
wherein when the transfer means is moved and brought into contact with the excising specimen, a mark formed on the transfer means and a mark formed in a region, which makes the excising specimen, on the specimen are measured and the transfer means is stopped in the case where a relative position between the marks is put in a predetermined condition.

23. A control method for a specimen preparation device, the method comprising steps of: mounting a specimen on a specimen stage; irradiating an ion beam by way of an ion beam optical system; transferring by way of transferring means, an excising specimen separated from the specimen by means of ion beam irradiation; and controlling the ion beam optical system with an arithmetic unit,
wherein when the transfer means is moved and brought into contact with the excising specimen, a mark formed on the transfer means and a mark formed in a region other than another region, which makes the excising specimen, on the specimen are measured and the transfer means is stopped in the case where a relative position between the marks is put in a predetermined condition.

24. A control method for a specimen preparation device, the method comprising steps of: mounting a specimen on a specimen stage; irradiating an ion beam by way of an ion beam optical system; transferring by way of transferring means, an excising specimen separated from the specimen by means of ion beam irradiation; holding the excising specimen with a specimen holder; and controlling the ion beam optical system with an arithmetic unit,
wherein when the excising specimen held on the transfer means is transferred to the specimen holder, a mark formed on the excising specimen and a mark formed on the specimen holder are measured and movement of the transfer means is stopped in the case where a relative position between the marks is put in a predetermined condition.

25. A control method for a specimen preparation device, the method comprising steps of: mounting a specimen on a specimen stage; irradiating an ion beam by way of an ion beam optical system; transferring by way of transferring means, an excising specimen separated from the specimen by means of ion beam irradiation holding the excising specimen with a specimen holder; and controlling the ion beam optical system with an arithmetic unit, wherein when the excising specimen held on the transfer means is transferred to the specimen holder, a mark formed on the transfer means for transfer of the excising specimen and a mark formed on the specimen holder are measured and movement of the transfer means is stopped in the case where a relative position between the marks is put in a predetermined condition.

* * * * *

UNITED STATES PATENT AND TRADEMARK OFFICE
CERTIFICATE OF CORRECTION

PATENT NO. : 8,710,464 B2
APPLICATION NO. : 13/203807
DATED : April 29, 2014
INVENTOR(S) : Yuichi Madokoro et al.

It is certified that error appears in the above-identified patent and that said Letters Patent is hereby corrected as shown below:

THE TITLE PAGE OF THE LETTERS PATENT, should read,

\*\* (87)   PCT Pub. No. WO2010/116428 \*\*

Signed and Sealed this
Sixth Day of January, 2015

Michelle K. Lee
*Deputy Director of the United States Patent and Trademark Office*